United States Patent [19]

Chaudhuri et al.

[11] Patent Number: 4,508,705

[45] Date of Patent: Apr. 2, 1985

[54] SKIN TREATMENT COMPOSITION

[75] Inventors: Dwaipayan Chaudhuri, Ashford; Malcolm R. Stebles, Maidenhead, both of England

[73] Assignee: Lever Brothers Company, New York, N.Y.

[21] Appl. No.: 165,453

[22] Filed: Jul. 2, 1980

[51] Int. Cl.$^3$ .............................. A61K 7/36; A61K 9/12
[52] U.S. Cl. ........................................ 424/47; 424/65; 424/66; 424/67; 424/68; 424/78
[58] Field of Search ................... 424/67, 66, 68, 65, 424/47

[56] References Cited

U.S. PATENT DOCUMENTS

| 3,146,170 | 8/1964 | Battista | 424/362 |
| 3,172,817 | 3/1965 | Leupold et al. | 424/65 |

FOREIGN PATENT DOCUMENTS

| 2263509 | 7/1974 | Fed. Rep. of Germany | 424/65 |
| 2453139 | 5/1975 | Fed. Rep. of Germany | 424/47 |
| 2510364 | 9/1975 | Fed. Rep. of Germany | 424/47 |
| 2703373 | 8/1977 | Fed. Rep. of Germany | 424/68 |
| 2168422 | 5/1973 | France | 424/65 |
| 2215937 | 8/1974 | France | 424/68 |
| 23863 | of 1914 | United Kingdom | 424/65 |
| 425059 | 3/1935 | United Kingdom | 424/65 |
| 1375781 | 9/1974 | United Kingdom | 424/65 |
| 1427861 | 3/1976 | United Kingdom | 424/68 |
| 2503963 | 8/1976 | United Kingdom | 424/47 |
| 1485373 | 9/1977 | United Kingdom | 424/47 |
| 1501862 | 2/1978 | United Kingdom | 424/47 |
| 1560401 | 2/1980 | United Kingdom | 424/68 |

Primary Examiner—Dale R. Ore
Attorney, Agent, or Firm—Milton L. Honig; James J. Farrell

[57] ABSTRACT

An antiperspirant composition for topical application to human skin comprises a moisture-absorbent water-insoluble polymer which is substantially dry to the touch when swollen with water, a surfactant having a melting point of from 30° to 75° C. and an organic solvent in which the polymer is substantially insoluble. The polymer has a water absorption value of at least 2, preferably 5 to 500. Preferred polymers are derived from anionic polyelectrolytes.

The antiperspirant composition can be packaged in a dispenser or other container such as a propellant pressurized aerosol device, a finger-operated pump spray device or a roll-ball applicator.

19 Claims, No Drawings

SKIN TREATMENT COMPOSITION

This application is a continuation of application Ser. No. 935,198, filed Aug. 21, 1978, now abandoned.

The invention relates to antiperspirant compositions for topical application to human skin. More particularly the invention relates to antiperspirant compositions which can be dispensed from valved aerosol containers or pump spray dispensers or roll ball applicators to be deposited onto the skin in particulate form, or as a film or layer.

These compositions are based on moisture-absorbent materials which are generally non-astringent in nature and which help to make the composition substantially non-staining and milder to the skin.

Conventional antiperspirant compositions traditionally contain an astringent, such as aluminium chlorhydrate, zirconium oxychloride aluminium hydroxychloride complex or zinc phenol sulphonate, which is believed to depress the formation of perspiration from sweat glands. These astringents are commonly applied to the skin in the form of an aerosol spray.

We have now devised an entirely new type of composition for limiting the manifestation of perspiration on the skin which does not necessarily require the use of astringent perspiration depressants, such as those exemplified above, and which can therefore reduce the irritating effect that astringents and their by-products sometimes produce. Therefore, instead of relying entirely on chemical suppression of perspiration at source, we employ a means whereby perspiration can be absorbed at the skin surface as soon as it is formed, thus maintaining the skin in an apparently dry condition. This is achieved by applying to the skin a composition containing a special polymer having a high capacity for absorbing superficial skin moisture, together with a substance which controls the moisture absorbing capacity of the polymer, which improves its adhesion to the skin and which enhance its superficial tactile properties. It follows that transfer of perspiration from the skin to adjacent clothing can also be limited or prevented completely by this means which is at least as effective as conventional astringent antiperspirant materials, but which does not suffer from the disadvantages associated with such materials.

Extensive laboratory investigations and in vivo trials involving human subjects have been directed to the problems of controlling the degree to which the polymer absorbs water and of enhancing the substantivity of the polymer to the skin and its superficial tactile properties.

Early investigations showed, for example, that although a polymer might intrinsically be capable of absorbing an amount of water equal to many times its own weight, the swelling of the polymer on the skin as it absorbed perspiration caused it to become obtrusive to the extent that the subject expressed a dislike of the 'feel' of the swollen polymer on the skin.

It was also observed that a film or layer of the polymer when applied to the skin lacked sufficient substantivity to remain intact on the skin over an extended period of time, for example during a working day. Body movement and contact by clothing adjacent to the treated area of skin tended to abraid the film or layer of polymer such that it would roll-up or flake-off the skin with consequent loss of antiperspirancy.

It was furthermore noted by human subjects that the 'feel' of the film or layer of the polymer lacked the desirable smoothness which was necessary if the presence of the polymer on the skin was to remain unobtrusive. A slight roughness of the film or layer of polymer would, for example, tend to 'catch' on adjacent clothing and skin: this was considered to be an undesirable attribute.

The problems of how to control moisture uptake, how to improve substantivity and how to improve 'feel' have now been solved by including a special surfactant in the composition.

The invention accordingly provides an antiperspirant composition comprising from 0.1 to 30% by weight of a moisture-absorbent water-insoluble polymer which is substantially dry to the touch when swollen with water and which has a water absorption value of at least 2, from 0.1 to 15% by weight of a surfactant having a melting point of from 30° to 75° C., and from 1 to 99.8% by weight of an organic solvent in which the polymer is substantially insoluble.

The invention also provides a process for preparing an antiperspirant composition which comprises mixing together the moisture-absorbent water-insoluble polymer, the surfactant and the organic solvent as herein defined.

The invention also provides a method for absorbing perspiration which comprises applying topically to the skin, particularly in the region of apocrine sweat glands, an antiperspirant composition as herein defined.

The moisture-absorbent water-insoluble polymer will generally have a water absorption value of at least two, preferably from 5 to 500 and most preferably from 10 to 50.

The water absorption value of a polymer is measured by spraying it in a finely divided dry state onto a tared filter paper using an anhydrous propellant as a vehicle. After allowing the propellant to evaporate, the filter paper is weighed again to give the dry weight of the polymer which has been deposited.

Water is then sprayed onto the reverse side of the filter paper until the deposited polymer is just wet to the touch and also appears wet when observing the reflectance of a beam of light directed onto the top surface of the polymer layer. The paper is weighed again to give the 'wet' weight of the polymer and hence the amount of water absorbed by the polymer.

The water absorption value is given by the weight of water absorbed by the polymer divided by the dry weight of the polymer.

The polymer is preferably chosen from one or more of the following polymers:
 (a) a cross-linked starch
 (b) other anionic polyelectrolytes, and
 (c) a base hydrolysed starch/polyacrylonitrile graft copolymer.

More specifically, an example of the cross-linked starch is a substantially water-insoluble cross-linked gelatinised starch, in which the degree of substitution of the cross-linking groups is 0.001 to 0.04, which is preferably, but not necessarily, substituted by ionic groups attached to the starch by ether linkages, these groups, when present, being associated with mono- or di-valent counterions.

Although the degree of substitution of the cross-linking groups can be relatively low, the cross-linked starch is substantially insoluble in water.

The cross-linking of the starch molecules may be effected by ether bridges of the formula —O—R—O—, where R is an aliphatic group, which may be substituted by one or more hydroxy groups, containing 1 to 10 carbon atoms. Preferably R is CH$_2$CH(OH)CH$_2$—, which is the case when the starch is cross-linked using epichlorhydrin as cross-linking agent.

The ionic groups, when present, preferably have the formula Z—R$^1$ and R$^1$ is an alkylene group having 1 to 5 carbon atoms and Z is an anionic group selected from carboxyl, sulphonic or phosphonic groups or a cationic group of the formula:

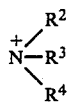

where R$^2$ is hydrogen or lower alkyl, and R$^3$ and R$^4$ are lower alkyl or are alkylene groups linked together to form a five or six-membered heterocyclic ring. Particularly suitable materials are those wherein R$^1$ is an alkylene group containing 1 or 2 carbon atoms and Z is —COO$^-$ and preferred materials are carboxymethylated cross-linked gelatinised starches.

When the polymer is substituted by ionic groups, the degree of substitution of the ionic groups will generally be at least 0.1 and is desirably at least 0.2 to obtain the preferred higher water absorption values.

When Z is an anionic group, the counterion preferably is an alkali metal, alkaline earth metal, ammonium or substituted ammonium ion. The substituted ammonium derivatives may be those in which one or more hydrogen atoms are replaced by C$_{1-4}$ alkyl or C$_{2-4}$ hydroxyalkyl groups or in which the nitrogen atom forms part of a heterocyclic ring. An example of such a substituted ammonium ion is tetramethylammonium. Preferred counterions when Z is an anionic group are the sodium, pottasium and ammonium ions. When Z is a cationic group, the counterion may be, for example, chloride, bromide or sulphate.

Particularly preferred absorbent materials of this invention are the sodium and ammonium salts of carboxymethylated epichlorhydrin cross-linked gelatinised starch having a water absorption value of at least 5 and being insoluble in water to the extent of at least 99% by weight. The sodium or ammonium salts are hereinafter referred to in the examples as "sodium cross-linked starch" or "ammonium cross-linked starch" respectively.

Cross-linked gelatinised starch can be prepared by the process described in our British Patent Application No. 2118/77.

Examples of the anionic polyelectrolyte, other than the cross-linked starches as hereinbefore defined, which are alternative polymers having a water absorption value of at least 2 are water-insoluble ionic complexes of a water-soluble anionic polyelectrolyte and a polyvalent metal cation having a valency of at least three, the cation being present in the amount of 0.01 to 5.0 milliequivalents per gram of polyelectrolyte.

The polyelectrolyte generally contains anionic groups, such as carboxylate, sulphonate, sulphate and phosphate groups or mixtures thereof. Preferably the polyelectrolyte is polyacrylic acid.

The cation is a transition metal, preferably aluminium, iron, chromium, zirconium, titanium or mixtures thereof. The cation is preferably present in the amount of 0.1 to 1.0 millequivalents per gram of polyelectrolyte.

A particularly preferred polyelectrolyte is polyacrylic acid having from 40 to 85% of its carboxylate groups neutralised, the cation being aluminium which is present in the amount of from 0.1 to 1.0 milliequivalents per gram of polyelectrolyte.

These polyelectrolytes and their preparation are further described in German Patent Application (DTOLS) No. 2 609 144 (National Starch and Chemical Corporation).

Further examples of the anionic polyelectrolyte are water-insoluble covalently cross-linked anionic polyelectrolytes.

The anionic polyelectrolytes can be water-soluble polyelectrolytes which are covalently cross-linked to render them insoluble yet capable of absorbing water.

Examples of these water-soluble anionic polyelectrolytes to be covalently cross-linked are natural polymers, such as anionic derivatives of starch and cellulose, and synthetic polymers such as carboxylic homopolymers or copolymers containing at least 20 mole percent carboxylic acid units such as polyacrylic acid.

Examples of the covalent cross-linking compounds which can be copolymerised with the polyelectrolytes are divinyl compounds, such as divinyl benzene, divinyl diethylene glycol diether, divinyl diphenyl silicone and divinyl sulphone; allyl compounds, such as triallyl cyanurate, trimethylol propane diallyl ether, allyl methacrylate, allyl acrylate, allyl crotonate, diallylphthalate, diallyl succinate and diallyl sucrose; polyfunctional acrylates and methacrylates, such as tetraethylene glycol diacrylate, triethylene glycol dimethacrylate, pentaerythritol tetra acrylate, ethylidene dimethylacrylate and trimethylol propane trimethacrylate; and polyfunctional arylamides and methacrylamides, such as N,N'-methylene bis-acrylamide and N,N'-methylene bismethacrylamide.

These water-insoluble covalently cross-linked anionic polyelectrolytes and their preparation are further described in Netherlands Patent Application No. 7 604 518 (National Starch and Chemical Corporation).

Any of the water-insoluble anionic polyelectrolyte complexes as herein described can be surface treated with a polyvalent metal cation to maximise absorption by the polymer particles of moisture.

The preferred polyvalent metal cations for surface treatment are aluminium, zirconium, chromium, titanium and zinc.

These surface-treated water-insoluble anionic polyelectrolyte complexes and their preparation are also further described in Netherlands Patent Application No. 7 604 518 (National Starch and Chemical Corporation).

An example of a surface treated anionic polyelectrolyte is National Starch Resyn 78-3803 which is potassium polyacrylate cross-linked with aluminium.

Examples of the base hydrolysed starch polyacrylonitrile graft copolymer are those comprising water-insoluble alkali metal salts of saponified gelatinised starch and saponified polyacrylonitrile in mole ratios of from 1:1.5 to 1:9. Copolymers such as these are identified and prepared by the methods set out in Journal of Applied Polymer Science, Volume 13, pages 2007–2017 (1969), and Volume 15, pages 3015–3024 (1971).

The moisture absorbent polymer should be in the form of a finely-divided powder having a particle size not greater than 100μ, preferably not greater than 60μ.

The quantity of the moisture absorbent polymer to be employed is generally at least 0.1, usually from 0.1 to 30% by weight of the composition, but the actual amount chosen will depend on the nature of that composition and the water absorption value of the polymer. Preferably, the amount of polymer is from 0.5 to 20%, most preferably from 1 to 15% by weight of the composition.

It is apparent that compositions containing less than 0.1% by weight of the composition of polymer are unlikely to perform effectively as antiperspirants, whereas where the polymer forms more than 30% by weight of the composition, the composition may be difficult to dispense or the amount of polymer deposited on the skin when the composition is used as an antiperspirant may be excessive leading to poor consumer acceptance.

The composition also comprises a surfactant having a melting point of from 30° to 75° C.

Preferred examples of the surfactant are cetyl alcohol, iso-cetyl alcohol, stearyl alcohol, stearic acid, palmitic acid, glycerol monolaurate, ethoxylated fatty alcohols and mixtures thereof.

The most preferred surfactants are nonionic surfactants.

It is important to ensure that the chosen surfactant has a melting point within the defined range, since it is the surfactant which influences the ability of the polymer to absorb moisture, improves its substantivity to the skin and enhances the feel of the polymer on the skin. It has for example been shown that when the surfactant is one which has a melting point of less than 30° C., it adversely affects the behaviour of the polymer on the skin in three ways. Firstly, the particles of the polymer in contact with the skin can, under certain circumstances, agglomerate; secondly, the substantivity of the polymer on the skin can be poor, and thirdly moisture uptake by the polymer on the skin can lack the necessary control to optimise both moisture uptake and swelling of the polymer.

It should be explained that agglomeration can occur in the presence of a low melting point surfactant in the following manner. The particles of polymer when first applied to the skin will usually form a smooth film, but as they absorb moisture, for example from perspiration, the particles will generally tend to migrate towards each other on the skin surface to form adhering groups of particles known as agglomerates. This is apparently due to the inability of the low melting point surfactant to hold the particles in place on the skin. As perspiration evaporates, the polymer particles revert to the dry state, but because of agglomeration a rough 'sand paper' texture results. The polymer now forms an abrasive textured layer on the skin which is unacceptable to the consumer.

It should also be explained that the agglomerated polymer exhibits poor substantivity to the skin, because the agglomerates are heavier than the individual particles of the polymer and hence are more easily dislodged from the skin.

It should also be explained that when the surfactant has a melting point of less than 30° C., it is unable to reduce moisture uptake from the skin by particles of a polymer having a high water absorption value. It is therefore likely that excessive swelling of the polymer will lead to the formation of an obtrusive layer on the skin which is unacceptable because the presence of the film can then be felt by the user.

It has also been shown that if the melting point of the surfactant exceeds 75° C., it can coat the polymer particles on the skin to such an extent that moisture uptake by the polymer is severely hampered, with the result that there can be inadequate control of perspiration.

It follows that the choice of a surfactant which has a melting point of from 30° to 75° C. restricts mobility of the polymer particles on the skin as moisture is absorbed and maintains adequate adherences of the particles to the skin without excessively restricting their ability to absorb moisture from the skin.

The quantity of surfactant to be employed is generally from 0.1 to 15%, preferably from 0.1 to 10% by weight of the composition.

Compositions containing less than 0.1% by weight of a surfactant will tend to be less substantive to the skin than is desirable and will also lack the sufficient control of moisture uptake and so can lead to a film or layer of polymer on the skin which is too obtrusive on absorption of moisture. Compositions containing more than 15% by weight of a surfactant can contribute excessively to the apparent greasiness of the film or layer of polymer on the skin and can severely restrict absorption of moisture with consequent loss of effectiveness of the antiperspirant composition.

The composition also comprises an organic solvent in which the polymer is substantially insoluble. The function of the solvent is to provide the composition with sufficient mobility to distribute the polymer conveniently and uniformly on the skin. The solvent should, however, be capable of subsequently evaporating from the skin within a few minutes, so that the composition is then dry to the touch, without residual 'wetness' or 'greasiness' derived from the solvent. The solvent should accordingly have a boiling point no higher than 150° C., preferably no higher than 100° C.

Examples of solvents are ethyl alcohol, methylene chloride, isopropyl alcohol, ethylene glycol monomethyl ether, low boiling liquid paraffins, such as pentane, hexane, heptane and octane, volatile silicones such as linear and cyclic polydimethyl siloxanes. The solvent can also be a propellant such as trichlorofluoromethane, dichlorodifluoromethane, dichlorotrifluoroethane, monochlorodifluoromethane, trichlorotrifluoroethane, propane, butane, isobutane, dimethylether and carbon dioxide.

The solvent will generally comprise at least 1%, preferably from 55 to 99.8% by weight of the composition, the amount actually selected generally forming the balance of the composition after accounting for the polymer, the surfactant and any optional ingredients that may also be included in the formulation.

The composition can also optionally comprise an emollient which, if present, is preferably a non-hydroxylic emollient, although certain hydroxylic emollients can be employed. The emollient will generally have a melting point of less than 20° C.

Preferred examples of non-hydroxylic emollients are isopropylmyristate, isopropyl palmitate and dibutylphthalate. Preferred examples of hydroxylic emollients are 2-ethyl-1,3-hexane diol and hexylene glycol.

The quantity of emollient when included in the composition is generally up to 30%, preferably from 5 to 20%, most preferably from 8 to 10% by weight of the composition.

The composition can also optionally comprise a suspending agent which, if present, is one which is hydrophobically treated, for example, hydrophobically treated montmorillonite clays.

It should be explained that montmorillonite clays are clays that contain the mineral montmorillonite, and are characterised by having an expanded lattice. An example is bentonite.

Bentonite is colloidal hydrated aluminium silicate obtained from montmorillonite and has the formula $Al_2O_3 4SiO_2 \cdot H_2O$. A more detailed discussion of bentonites can be found in the Kirk-Othmer Encyclopedia of Chemical Technology, 2nd Edition, Vol 3, (1964) pp 339–360, published by Interscience Publishers.

Examples of hydrophobically treated bentonites are BENTONE 27 which has the structure

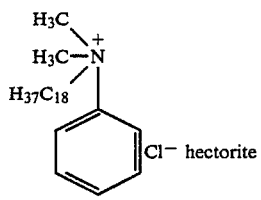

and BENTONE 38 which has the structure

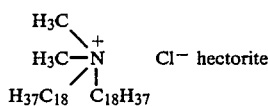

BENTONITES are available from the National Lead Company. Montmorillonite clays can also be prepared synthetically and can be treated with long chain amines to render them hydrophobic. An example is the hydrophobic form of LAPONITE available from Laporte Industries.

Further examples of suspending agents are Acrawax C (an ethylene diamine condensate with 2 mols stearic acid), zinc ricinoleate, zinc stearate and Aerosil 200 (a pyrogenic silica) and sodium stearate.

The quantity of suspending agents that can optionally be employed is generally up to 8% by weight of the composition.

The composition can also optionally comprise a deodorant. Examples of deodorants are sodium carbonate, sodium bicarbonate, aluminium chlorhydrate, aluminium sulphate and zinc ricinoleate. It will be appreciated that astringent aluminium salts such as the sulphate and chlorhydrate will, if present, also function as antiperspirants.

The deodorant, if present, can comprise from 0.1 to 20% by weight of the composition.

The antiperspirant composition can take the form of a propellant based aerosol product or it can be employed in the absence of a propellant in a pump spray dispenser. Alternatively, the antiperspirant composition can be a lotion containing the polymer suspended or dispersed therein for direct application to the skin with a swab or with the use of a roll-ball applicator.

The invention accordingly also comprises an applicator or other container containing the antiperspirant composition as herein defined.

Compositions of the invention can be prepared by mixing together the polymer, the surfactant and the solvent and optional ingredients to provide a homogeneous dispersion of the solid particulate polymer in a liquid phase.

According to a preferred process, when the solvent comprises an aerosol propellant and a suspending agent is included, the suspending agent is first sheared with the propellant and then the mixture is blended with the other components previously filled into aerosol containers.

The compositions of the invention can be employed as antiperspirants to reduce or eliminate perspiration as it appears at the skin surface.

According to a preferred method, the composition is applied to the skin, in particular where apocrine sweat glands are abundant, for example in the axillae, and in the genital and anal regions of the body, the film, layer or deposit or polymer so formed providing a means whereby perspiration is absorbed as it reaches the skin surface without the polymer becoming sticky when swollen with the moisture present in perspiration.

The invention is further illustrated by reference to the following Examples.

EXAMPLE 1

This example illustrates a propellant based antiperspirant composition according to the invention.

The formulation of the composition was as follows:

|  | % w/w |
|---|---|
| Cetyl alcohol (surfactant) | 1 |
| Bentone 38 (suspending agent) | 0.6 |
| Isopropyl myristate (emollient) | 2 |
| Ethanol (solvent) | 0.3 |
| "Ammonium cross-linked starch" (polymer) | 3.5 |
| Sodium bicarbonate (deodorant) | 1.5 |
| Trichlorofluoromethan: Propellant 11 (solvent) | 45.55 |
| Monochlorodifluoromethane: Propellant 12 (solvent) | 45.55 |

In preparing this composition, the suspending agent was first milled with the propellant and this mixture was then blended with the other ingredients of the composition which had already been filled into aerosol containers. The containers were then fitted with conventional aerosol valves.

This composition when sprayed onto the axillae provided a sufficient protection against the appearance of perspiration for a period of at least 8 hours. The layer of polymer remained in close adherence to the skin and had a pleasant, smooth and unobtrusive feel. It was not noticeable when swollen with perspiration moisture and did not transfer to adjacent clothing.

EXAMPLE 2

Example 1 was repeated using a formulation containing the following ingredients:

|  | % w/w |
|---|---|
| Aluminium chlorhydrate | 1.5 |
| "Ammonium cross-linked starch" | 2.5 |
| Bentone 38 | 0.36 |
| Cetyl alcohol | 0.5 |
| Isopropyl myristate | 1.8 |
| Ethanol | 0.18 |
| Perfume | 0.44 |
| Propellant 11/12 (50:50) to | 100 |

EXAMPLE 3

Example 1 was repeated using a formulation containing the following ingredients:

|  | % w/w |
|---|---|
| "Ammonium cross-linked starch" | 1 |
| Glycerol monolaurate (surfactant) | 1 |
| Bentone 38 | 0.12 |
| Isopropyl myristate | 0.6 |
| Ethanol | 0.06 |
| Cetyl alcohol | 0.5 |
| Perfume | 0.44 |
| Propellant 11/12 (50:50) to | 100 |

EXAMPLE 4

Example 1 was repeated using a formulation containing the following ingredients:

|  | % w/w |
|---|---|
| "Ammonium cross-linked starch" | 3 |
| Isopropyl myristate | 5 |
| Ethanol | 20 |
| Bentone 27 (suspending agent) | 1.5 |
| Cetyl alcohol | 0.5 |
| Propellant 11/12 (50:50) to | 100 |

EXAMPLE 5

Example 1 was repeated using a formulation containing the following ingredients:

|  | % w/w |
|---|---|
| "Sodium cross-linked starch" | 3 |
| Isopropyl myristate | 4 |
| Ethanol | 13.5 |
| Bentone 27 | 1.5 |
| Cetyl alcohol | 1 |
| Propellant 11/12 (50:50) to | 100 |

EXAMPLE 6

This example illustrates a formulation which is suitable for dispensing by means of a finger operated pump spray device.

The formulation of the composition was as follows:

|  | % w/w |
|---|---|
| "Sodium cross-linked starch" | 15 |
| Industrial methylated spirit (solvent) | 70.12 |
| Isopropyl myristate | 11.9 |
| Bentone 27 | 1.7 |
| Cetyl alcohol | 1.28 |

EXAMPLE 7

Example 6 was repeated using the following formulation:

|  | % w/w |
|---|---|
| "Ammonium cross-linked starch" | 15 |
| Industrial methylated spirit | 60.12 |
| Isopropyl myristate | 11.9 |
| Bentone 27 | 1.7 |
| Cetyl alcohol | 1.28 |

-continued

|  | % w/w |
|---|---|
| Water | 10 |

EXAMPLE 8

Example 6 was repeated using the following formulation:

|  | % w/w |
|---|---|
| National Starch Resyn 78-3803 (polymer) | 7.5 |
| Industrial methylated spirit | 70.12 |
| Isopropyl myristate | 14.4 |
| Bentone 27 | 1.7 |
| Cetyl alcohol | 1.28 |

EXAMPLE 9

Example 6 was repeated using the following formulation:

|  | % w/w |
|---|---|
| "Sodium cross-linked starch" (polymer) | 15 |
| Industrial methylated spirit | 70.12 |
| Isopropyl myristate | 11.9 |
| Bentone 27 | 1.7 |
| Lauric acid monoglyceride (surfactant) | 1.28 |

EXAMPLE 10

Example 6 was repeated using the following formulation:

|  | % w/w |
|---|---|
| National Starch Resyn 78-3803 | 7.5 |
| Industrial methylated spirit | 74 |
| Isopropyl myristate | 15 |
| Bentone 38 | 0.5 |
| Cetyl alcohol | 0.5 |
| Zinc ricinoleate (suspending agent and deodorant) | 2.5 |

EXAMPLE 11

Example 6 was repeated using the following formulation:

|  | % w/w |
|---|---|
| "Sodium cross-linked starch" | 15 |
| Industrial methylated spirit | 70.12 |
| Isopropyl myristate | 11.9 |
| Cetyl alcohol | 1.28 |
| Acrawax C (suspending agent) | 1.7 |

EXAMPLE 12

This example illustrates a formulation which is suitable for dispensing from a roll-ball applicator.

The formulation of the composition was as follows:

|  | % w/w |
|---|---|
| National Starch Resyn 78-3803 | 7.5 |
| Industrial methylated spirit | 67.61 |
| Isopropyl myristate | 14.4 |
| Bentone 27 | 1.7 |

-continued

| | % w/w |
|---|---|
| Cetyl alcohol | 1.28 |
| Water | 7.51 |

EXAMPLE 13

Example 12 was repeated using the following formulation:

| | % w/w |
|---|---|
| National Starch Resyn 78-3803 | 7.5 |
| Industrial methylated spirit | 60.1 |
| Isopropyl myristate | 14.4 |
| Bentone 27 | 1.7 |
| Cetyl alcohol | 1.28 |
| Water | 15.02 |

EXAMPLE 14

Example 12 was repeated using the following formulation:

| | % w/w |
|---|---|
| "Ammonium cross-linked starch" | 10 |
| Industrial methylated spirit | 71.25 |
| Isopropyl myristate | 15.0 |
| Bentone 38 | 1.5 |
| Cetyl alcohol | 1.5 |
| Water | 0.5 |

EXAMPLE 15

Example 12 was repeated using the following formulation:

| | % w/w |
|---|---|
| "Sodium cross-linked starch" | 15 |
| Industrial methylated spirit | 70 |
| Isopropyl myristate | 12 |
| Bentone 38 | 0.5 |
| Cetyl alcohol | 1.0 |
| Zinc stearate (suspending agent) | 1.5 |

EXAMPLE 16

Example 12 was repeated using the following formulation:

| | % w/w |
|---|---|
| National Starch Resyn 78-3803 | 7.5 |
| Industrial methylated spirit | 74 |
| Isopropyl myristate | 15 |
| Bentone 38 | 0.5 |
| Cetyl alcohol | 0.5 |
| Sodium stearate | 2.5 |

The antiperspirant compositions described herein and in particular in each of Examples 2 to 16, as well as that of Example 1, when applied to the skin, each provide a tenacious, skin substantive film which resists dislodgement by the user if the surface is rubbed, in that it does not flake or roll-up. The film also has a considerable capacity for absorbing skin moisture and remains dry and non-sticky and does not disintegrate when swollen with water present in skin moisture. The film furthermore has a pleasant silky smooth feel which is unobtrusive even when the polymer is swollen with perspiration moisture.

The film also has the ability to regenerate by losing absorbed moisture by evaporation so that it is again ready to absorb further skin moisture.

What is claimed is:

1. An antiperspirant composition having a solid phase and a liquid phase, the solid phase comprising
   (i) from 0.1 to 30% by weight of the composition of a moisture-absorbent water-insoluble polymer which is substantially dry-to-the-touch when swollen with water and which has a water absorption value of at least 2 and which is selected from the group consisting of
   (a) a cross-linked gelatinised starch in which the degree of substitution of the cross-linking groups is 0.001 to 0.04;
   (b) an ionic complex of a water-soluble anionic polyelectrolyte and a polyvalent metal cation having a valency of at least three, the cation being present in the amount of from 0.01 to 5 milliequivalents per g polyelectrolyte;
   (c) a covalently cross-linked anionic olyelectrolyte wherein the anionic polyelectrolyte is selected from the group consisting of water-soluble derivatives of starch, water-soluble derivatives of cellulose, carboxylic homopolymers and copolymers containing at least 20 mole percent carboxylic acid units; and
   (d) mixtures thereof;
and the liquid phase comprising:
   (ii) from 0.1 to 15% by weight of the composition of a substantially water-insoluble surfactant having a melting point of from 30° to 75° C.; and
   (iii) from 1 to 99.8% by weight of the composition of an organic solvent in which the polymer is substantially insoluble.

2. The antiperspirant composition of claim 1, which further comprises a deodorant effective amount of zinc ricinoleate.

3. The antiperspirant composition of claim 1, wherein the cross-linked gelatinised starch is substituted by ionic groups attached to the starch by ether linkages, which groups are associated with mono- or di-valent counterions.

4. The antiperspirant composition of claim 1, wherein, in the cross-linked starch, the cross-linking is effected by ether bridges of the formula —O—R—O—, where R is an aliphatic group containing 1 to 10 carbon atoms.

5. The antiperspirant composition of claim 3, wherein the ionic groups have the structure Z—$R^1$—, where $R^1$ is an alkylene group having from 1 to 5 carbon atoms and Z is an anionic group selected from carbonyl, sulphonic, and phosphonic groups, and a cationic group having the structure:

where $R^2$ is selected from hydrogen and lower alkyl groups, and $R^3$ and $R^4$ are selected from lower alkyl and alkylene groups linked together to form a five or six membered heterocyclic ring.

6. The antiperspirant composition of claim 3, wherein the ionic groups are anionic groups and the counterions are chosen from alkali metal, alkaline earth metal, ammonium and substituted ammonium ions.

7. The antiperspirant composition of claim 1, wherein the anionic groups of the water-soluble anionic polyelectrolyte are chosen from carboxylate, sulphonate, sulphate, phosphate and mixtures thereof.

8. The antiperspirant composition of claim 7, wherein the polyelectrolyte is polyacrylic acid.

9. The antiperspirant composition of claim 1, wherein the polyvalent metal cation having a valency of at least three is aluminium.

10. The antiperspirant composition of claim 1, wherein the carboxylic acid unit of the covalently cross-linked anionic polyelectrolyte co-polymer is polyacrylic acid.

11. The antiperspirant composition of claim 1, wherein the covalent compound with which the anionic polyelectrolyte is cross-linked is selected from divinyl compounds, alkyl compounds, polyfunctional acrylates and methacrylates, and polyfunctional acrylamides and methacrylamides.

12. The antiperspirant composition of claim 1, wherein the anoinic polyelectrolyte has been surface treated with a polyvalent metal cation.

13. The antiperspirant composition of claim 1, wherein the polymer has a water absorption value of from 5 to 500.

14. The antiperspirant composition of claim 1, wherein the surfactant is chosen from cetyl alcohol, iso-cetyl alcohol, stearyl alcohol, stearic acid, palmitic acid, glycerol monolaurate, ethoxylated fatty alcohols and mixtures thereof.

15. The antiperspirant composition of claim 1, wherein the organic solvent is a propellant.

16. The antiperspirant composition of claim 1, wherein the organic solvent is chosen from ethyl alcohol, methylene chloride, isopropyl alcohol, ethylene glycol monomethyl ether, pentane, hexane, heptane, octane, linear and cyclic polydimethyl siloxane and mixtures thereof.

17. An applicator or other container containing an antiperspirant composition as claimed in claim 1.

18. A process for preparing the antiperspirant composition of claim 1, which comprises mixing the moisture absorbent polymer with the surfactant and the solvent.

19. A method for absorbing perspiration from human skin, which comprises applying to the skin the antiperspirant composition of claim 1.

* * * * *